United States Patent [19]
Forrester

[11] Patent Number: 5,400,637
[45] Date of Patent: Mar. 28, 1995

[54] SYSTEM AND METHOD OF CHECKING CALIBRATION OF BREATH ALCOHOL MEASURING INSTRUMENT WITH BAROMETRIC PRESSURE COMPENSATION

[75] Inventor: Glenn C. Forrester, Oakland, Calif.

[73] Assignee: Intoximeters, Inc., St. Louis, Mo.

[21] Appl. No.: 172,598

[22] Filed: Dec. 21, 1993

[51] Int. Cl.⁶ ............................................ G01N 33/00
[52] U.S. Cl. .................................... 73/1 G; 73/23.3; 422/84; 436/9; 436/900
[58] Field of Search .............. 73/1 G, 23.21, 23.27, 73/23.3; 128/719; 422/84; 436/9, 900

[56] References Cited

U.S. PATENT DOCUMENTS

| | | |
|---|---|---|
| 3,847,551 | 11/1974 | Hutson . |
| 3,951,855 | 4/1976 | Principe et al. . |
| 4,278,636 | 7/1981 | Voigt et al. . |
| 4,487,055 | 12/1984 | Wolf . |
| 4,671,298 | 6/1987 | Babb et al. . |
| 4,749,553 | 6/1988 | Lopez et al. . |
| 5,134,875 | 8/1992 | Jensen et al. ................. 73/1 G |

FOREIGN PATENT DOCUMENTS

| | | | |
|---|---|---|---|
| 8808979 | 11/1988 | WIPO | ................. 422/84 |
| 9207261 | 4/1992 | WIPO | ................. 436/9 |

OTHER PUBLICATIONS

*Intoximeter/Caldetect Newsletter*—Selecting an Alcohol Standard for Breath Testing Instruments–No. 2.

Primary Examiner—Hezron E. Williams
Assistant Examiner—Daniel S. Larkin
Attorney, Agent, or Firm—Polster, Lieder, Woodruff & Lucchesi

[57] ABSTRACT

A system and method for checking the calibration of a breath alcohol measuring instrument by the use of alcohol standards all containing substantially identical concentrations of alcohol and the use of a calculator which generates an expected measured value for the standard based on the known alcohol concentration and current atmospheric pressure.

4 Claims, 1 Drawing Sheet

SYSTEM AND METHOD OF CHECKING CALIBRATION OF BREATH ALCOHOL MEASURING INSTRUMENT WITH BAROMETRIC PRESSURE COMPENSATION

TECHNICAL FIELD

This invention relates to a method of checking the calibration of a breath alcohol measuring instrument by means of a dry, pressurized ethanol standard.

BACKGROUND OF THE INVENTION

When breath alcohol measuring instruments are used for forensic purposes, it is particularly important to establish that each measurement is accurate. The U.S. Department of Transportation (DOT), for example, requires 95% accuracy for a breath alcohol instrument which is used to establish the blood alcohol level of highway drivers.

In order to establish the accuracy of an instrument, its calibration is checked periodically and a notation is made that its calibration remains within legal tolerances. Ideally, the calibration check is made every time a suspect's breath is checked and its adherence to calibration is recorded automatically.

There has been long recognition that the reading of a standard is subject to several variables. The expected value of simulator (wet gas) must be at 34° C. to supply a proper sample, while dry gas standards must be adjusted for barometric pressure. Calibration of such instruments with dry standards has been proposed by taking into account this variable. Such approaches recalibrate the instrument each time a standard is run. The present invention is not concerned with recalibrating the instrument, but rather with checking that the instrument is calibrated accurately.

The use of dry pressurized gas calibration standards for breath alcohol instruments has long been known. Hutson, U.S. Pat. No. 3,847,551, discloses using such a standard to overcome many of the complications inherent in calibrating and checking the calibration of a breath alcohol instrument. It has been found, however, that changes in atmospheric pressure (barometric pressure) produce a change in the reading given with the dry pressurized Standard, even when the instrument is properly calibrated and therefore gives accurate measurements when measuring breath alcohol. Therefore, changes in barometric pressure can make an instrument appear to be out of calibration when it in fact is properly calibrated, or conversely can make an instrument appear to be in calibration when it is not. Changes in atmospheric pressure may be caused not only by changes in elevation, but by changes in pressure in weather. Although the pressure changes caused by elevational differences are constant with time, weather changes can produce apparent, spurious, changes in calibration amounting to as much as five percent.

SUMMARY OF THE INVENTION

One of the objects of this invention is to provide a means of checking the calibration of a breath alcohol measuring instrument which compensates for changes in atmospheric pressure.

Another object is to provide such a means which is simple to use and which requires manual entry of no data in order to provide an indication of proper calibration values.

Other objects will be apparent to those skilled in the art in light of the following description and accompanying drawings.

In accordance with one aspect of this invention, generally stated, a method of checking the calibration of a breath alcohol measuring instrument is provided comprising producing a pressurized dry standard having a preselected concentration of alcohol in a carrier gas, introducing a preselected quantity of the standard into the instrument, and comparing the output of the instrument with a number (value) calculated from the current atmospheric pressure and the preselected alcohol concentration. The calculated number is produced by an calculator device which includes a pressure transducer for producing a digital signal representative of present barometric pressure and a simple arithmetic unit for multiplying that digital signal by a predetermined factor. Because all standards are produced to the same alcohol concentration, the predetermined factor can be factory preset and no user input is required in order to produce the calculated value. Thus, if the standard produces a nominal reading of 100 in a properly calibrated instrument, and barometric pressure causes the instrument to produce a reading of 97, the calculator device will likewise show an expected value of 97, thereby indicating that the measuring instrument is in calibration. Even if the instrument shows a reading of 94 under these conditions, it is still within 5% calibration.

DESCRIPTION OF THE PREFERRED EMBODIMENT

Figure 1:
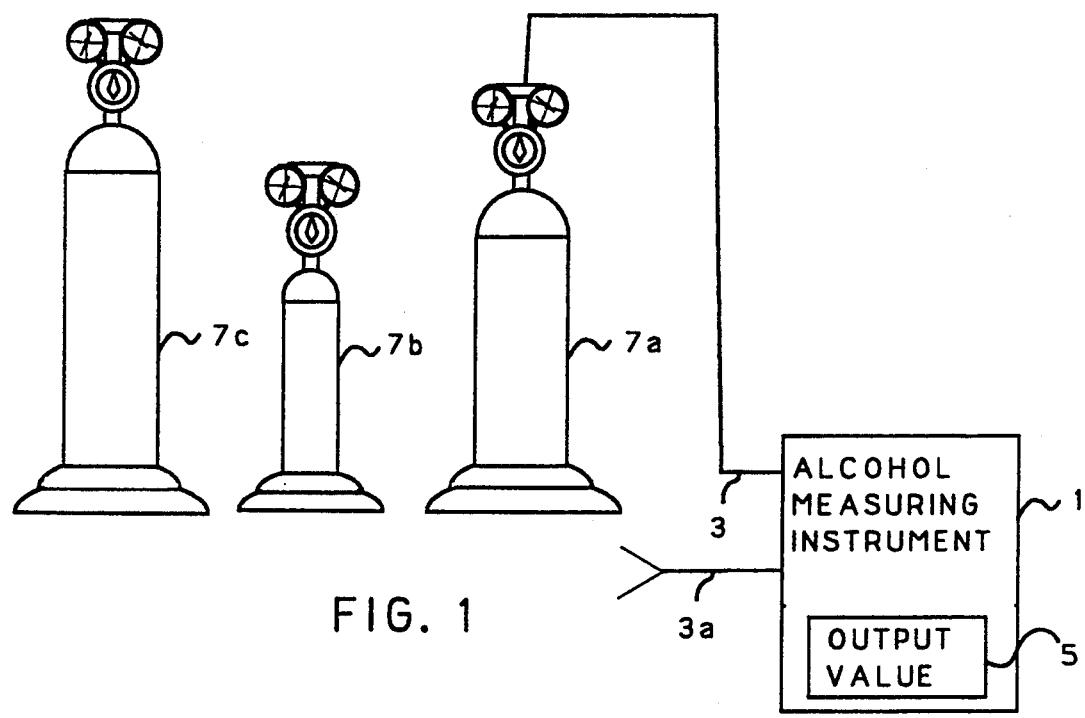
FIG. 1 is a representation of a system in accordance with the present invention, including multiple substantially identical standards, a breath alcohol measuring instrument, and a pressure compensating calculator device.
Figure 2:
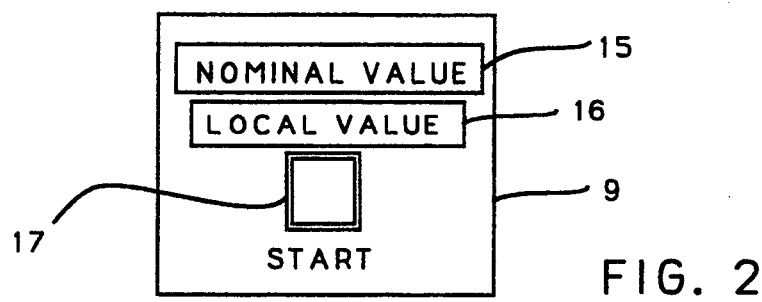
FIG. 2 is a diagrammatic representation of a calculator device for producing an expected value to be produced by a breath alcohol measuring instrument at a current atmospheric pressure in accordance with the present invention.
Figure 3:
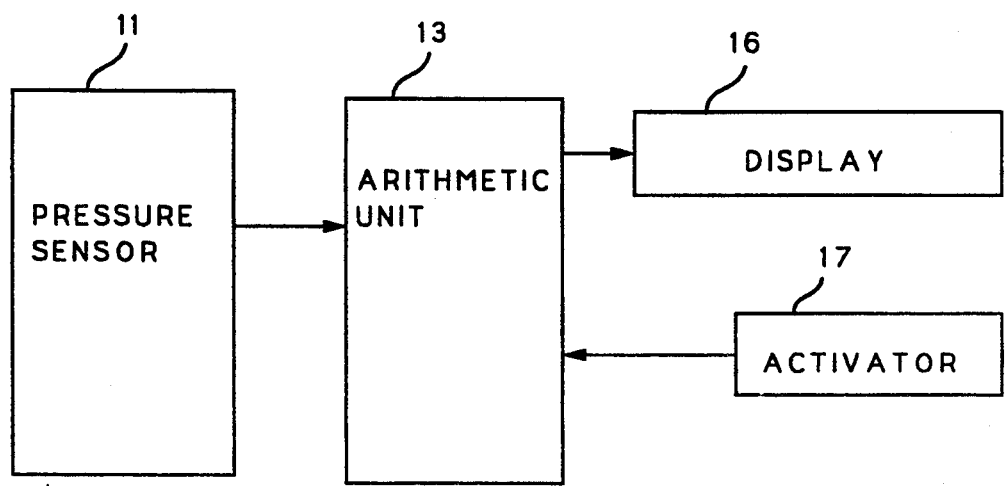
FIG. 3 is a diagrammatic representation of the interacting components of the calculator device of FIG. 2.

Referring now to the drawing for one illustrative embodiment of the present invention, reference numeral 1 indicates a standard breath alcohol measuring instrument, illustratively a fuel cell-based instrument sold by Intoximeters, Inc., under the trademark ALCO-SENSOR. The instrument 1 includes one or more inlets 3 and 3a for admitting a metered quantity of breath and a metered quantity of a test gas, an alcohol measuring portion, illustratively a fuel cell, and a display 5 for indicating the measured amount of alcohol in the breath sample or gas standard. It will be understood that the exact construction of the instrument 1 is not critical to the present invention, and any instrument which gives a reading of breath alcohol which accurately reflects blood alcohol concentration independent of ambient atmospheric pressure is usable with the present invention.

In accordance with the present invention, the gas standard is provided in pressurized containers 7a, 7b, and 7c, the gas in each container 7 containing a single standardized concentration of alcohol. Preferably, the standard is produced in accordance with the aforementioned Hutson patent, U.S. Pat. No. 3,847,551, with a concentration of alcohol of two hundred twenty-five parts per million (225 ppm), the remainder being argon. It has been found that by gravimetric filling techniques the percent of this nominal value. Containers of sizes ranging from a single sample size to many liters may be utilized interchangeably, so long as the concentration of alcohol in each is the same standardized value.

In further accordance with the present invention, a pressure sensing calculator 9 is provided. The calculator 9 includes a pressure sensor 11 connected to an arithmetic unit 13. The pressure sensor 11 is preferably a commercially available solid state absolute pressure transducer. The arithmetic unit 13 uses the known concentration of alcohol in the standard gas and a value empirically determined from the pressure sensor to calculate the expected local value the alcohol .measuring instrument 1 should display at 5 when the standard gas is tested. This expected value is displayed as indicated at 16 in response to activation of a manual push button 17. For convenience, the nominal value produced at sea level is permanently-displayed as shown at 15. It has been found that the correction factor applied on account of atmospheric pressure can be closely approximated by Boyle's law, and that a linear correction can therefore be made by multiplying the expected value at standard sea-level barometric pressure (corresponding to a barometric pressure of 760 mm of mercury) by a number equal to the measured barometric pressure divided by standard sea-level pressure.

In use in the field,, the operator attaches the measuring instrument 1 to a container 7a containing the standard, and activates the instrument 1 to take a measurement. The output value at 5 is recorded. Immediately before or after measuring the standard, the start button 17 is activated, and the expected value displayed at 15 is also recorded. If the value of the standard is within 5% of the expected value, the instrument 1 is properly calibrated. The suspect then breaths into the instrument 1 and the measured alcohol level is recorded.

Numerous variations, within the scope of the appended claims, will be apparent to those skilled in the art in light of the foregoing description and accompanying drawings.

I claim:

1. In combination, a breath alcohol measuring instrument, a plurality of dry pressurized gas standards for checking calibration of the instrument, each of the standards containing a preselected concentration of alcohol, the concentration in each of the standards being identical within a tolerance allowed the instrument, and a calculating means for calculating an expected value to be produced by the measuring instrument when a predetermined amount of the standard is measured by the instrument, the calculating device means comprising a pressure transducer means for producing a signal dependent on atmospheric pressure and an arithmetic unit means for producing the expected value from the signal and a predetermined factor based on the preselected concentration of alcohol.

2. The combination of claim 1 wherein the concentration of alcohol in each of the standards varies by less than plus or minus five percent.

3. A method of checking calibration of a breath alcohol measuring instrument, the instrument producing an output representative of blood alcohol, the output being substantially independent of atmospheric pressure, the method comprising a step of providing a plurality of containers containing dry pressurized gas standards, each of the standards containing a preselected concentration of alcohol, the concentration of alcohol in each being identical within the tolerance allowed the instrument, a step of using one of the standards with the instrument to produce an output, and a step of calculating an expected value to be produced by the measuring instrument when a predetermined amount of the standard is measured by the instrument, the calculating step comprising producing a pressure signal dependent on atmospheric pressure and deriving an expected value from the pressure signal and a predetermined factor based on the preselected concentration of alcohol.

4. The method of claim 3 wherein the concentration of alcohol in each of the standards varies by less than plus or minus five percent.

* * * * *